US010173969B2

(12) United States Patent
Jaeger et al.

(10) Patent No.: US 10,173,969 B2
(45) Date of Patent: Jan. 8, 2019

(54) PRODUCTION OF ANILINE VIA ANTHRANILATE

(71) Applicant: Covestro Deutschland AG, Leverkusen (DE)

(72) Inventors: Gernot Jaeger, Erkelenz (DE); Jorgen Magnus, Dusseldorf (DE); Amgad Salah Moussa, Cologne (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/120,163

(22) PCT Filed: Feb. 19, 2015

(86) PCT No.: PCT/EP2015/053524
§ 371 (c)(1),
(2) Date: Aug. 19, 2016

(87) PCT Pub. No.: WO2015/124686
PCT Pub. Date: Aug. 27, 2015

(65) Prior Publication Data
US 2017/0066713 A1  Mar. 9, 2017

(30) Foreign Application Priority Data

Feb. 20, 2014 (EP) .................................. 14155937
Dec. 5, 2014 (EP) .................................. 14196431

(51) Int. Cl.
C12P 7/40 (2006.01)
C12P 13/00 (2006.01)
C07C 209/68 (2006.01)
C07C 209/78 (2006.01)
C07C 209/84 (2006.01)
C07C 263/10 (2006.01)

(52) U.S. Cl.
CPC .......... C07C 263/10 (2013.01); C07C 209/68 (2013.01); C07C 209/78 (2013.01); C07C 209/84 (2013.01); C12P 7/40 (2013.01); C12P 13/00 (2013.01); C12P 13/001 (2013.01)

(58) Field of Classification Search
CPC ... C07C 209/68; C07C 209/78; C07C 209/84; C07C 263/10; C12P 13/00; C12P 13/001; C12P 7/40
See application file for complete search history.

(56) References Cited

FOREIGN PATENT DOCUMENTS

| EP | 2660313 A1 | 11/2013 |
| JP | 2013230993 | * 11/2013 |
| RU | 2006115439 | * 11/2007 |
| WO | 2011050326 A1 | 4/2011 |
| WO | 2013103894 A1 | 7/2013 |

OTHER PUBLICATIONS

English Translation of JP2013230993, pp. 1-9 (Year: 2013).*
English Translation of RU2006115439 (also published as RU2327683), pp. 1-5 (Year: 2007).*
Wang et al.: "Insights on the Mechanism for synthesis of methylenedianiline from aniline and formaldehyde through HPLC-MS and isotope tracer studies", Chinese Chemical Letters, vol. 23, 2012, pp. 1254-1258.
Balderas-Hernandez et al.: "Metabolic engineering for improving anthranilate synthesis from glucose in *Escherichia coli*", Microbial Cell Factories, vol. 8, 2009, pp. 1-12.
Lindquist et al.: "Degradation of benzoic acid and its derivatives in subcritical water", Journal of Chromatography A, vol. 1218, 2011, pp. 2146-2152.
Davis et al.: "Nonenzymic decarboxylation of the aminobenzoates", Biochemical and Biophysical Research Communications, vol. 14, 1964, pp. 482-485.
Perego et al.: "Amorphous aluminosilicate catalysts for hydroxyalkylation of aniline and phenol", Applied Catalysis A: General, vol. 307, 2006, pp. 128-136.
Trejbal: "Syntheses of methylenedianilines over the zeolite catalysts", Petroleum & Coal, vol. 52, 2010, pp. 273-279.
Stevens et al.: "The decarboxylation of anthranilic acid", Canadian Journal of Chemistry, vol. 30, 1952, pp. 529-540.
Silva et al.: "Desarrollo y caracterizacion de cepas de *E. coli* disenadas para la produccion de antranilato", XI Congreso Nacional de Biotecnologia y Bioingenieria; 2005, Merida, Yucatan, Mexico, Conference paper (Abstract), 2005, p. 1.

* cited by examiner

Primary Examiner — Pancham Bakshi
Assistant Examiner — Mark R Luderer
(74) Attorney, Agent, or Firm — Donald R. Palladino

(57) ABSTRACT

The invention relates to a method for producing aniline, comprising the steps of: a) providing o-aminobenzoate, wherein said o-aminobenzoate comprises anthranilate anion and a suitable cation, b) converting said anthranilate anion to aniline by thermal decarboxylation in the presence or absence of a catalyst, c) extracting the aniline produced in step b) in an organic solvent at least once, and d) purifying the aniline produced in steps b) and c) by distillation, wherein said distillation produces aniline and a water phase.

37 Claims, 6 Drawing Sheets

PRODUCTION OF ANILINE VIA ANTHRANILATE

CROSS-REFERENCE TO RELATED APPLICATIONS

This Application is a National Phase Application of PCT/EP2015/053524, filed Feb. 19, 2015, which claims priority to European Application No. 14155937.7, filed Feb. 20, 2014, and European Application No. 14196431.2, filed Dec. 5, 2014, each of which being incorporated herein by reference.

FIELD

The invention relates to the field of producing aniline from raw material of renewable resources, such as e.g. biomass via a suitable microbial host followed by chemical conversion of an intermediate product to aniline.

BACKGROUND

Aniline is currently produced at several million tonnes per year from fossil raw materials, e.g. to produce polyurethanes. An aniline source based on renewable resources, also called "bioaniline", is strongly desired for the chemical industry in order to become independent from fossil resources. More importantly, there is a strong desire to reduce carbon dioxide ($CO_2$) emissions both for the chemical processes as well as by increasing the use of renewable resources in the raw materials. Bioaniline has a high potential of saving $CO_2$ emissions.

The invention further relates to engineering of microorganisms and production of aromatic compounds therefrom. In particular, the invention relates to the field of producing o-aminobenzoate (oAB) from renewable sources, such as e.g. biomass in a suitable recombinant microbial host. Typically a source containing a significant proportion of fermentable sugars is used. These sugars may include polysaccharides such as disaccharides, e.g. sucrose, or trisaccharides, e.g. kestose, as well as C-6 monosaccharides such as glucose, fructose or mannose and C-5 monosaccharides such as xylose and arabinose. A recombinant microbial strain capable of converting sugar to o-aminobenzoate (2-aminobenzoate, or tho-aminobenzoate, o-aminobenzoate, oAB) would enable the production of o-aminobenzoate from a wide range of renewable resources including sugar beet and sugar cane, starch-containing plants such as corn, wheat and rye, as well as lignocellulose e.g. from straw, wood or bagasse.

Currently, there is no renewable or biologically derived source of o-aminobenzoate or the corresponding acid available commercially and no known example of the large-scale biological production of o-aminobenzoate has been described. o-Aminobenzoate is a natural intermediate of the shikimate acid pathway and a precursor for the biosynthesis of the aromatic amino acid L-tryptophane. The biosynthetic pathway to o-aminobenzoate is relatively well understood in both prokaryotes and eukaryotes. A chemical conversion of o-aminobenzoate to aniline can be achieved. Current production methods of aniline rely on chemical synthesis from petroleum-derived raw-materials. Such petroleum-derived raw materials are not renewable as opposed to raw materials which are renewable, such as the renewable resource "biomass". Several chemical steps involved in the chemical synthesis result in high production costs of the chemicals. The conventional chemical synthesis of aniline can be associated with hazardous intermediates, solvents, and waste products which can have substantial impacts on the environment. Non-specific side-reactions on the aromatic-ring result in the reduction of the product yield. Petroleum-derived raw materials are influenced by cost fluctuations resulting from the global petroleum price.

WO 2013/103894 A1 discloses a method of producing aromatic amines via biologically-derived p-aminobenzoic acid (4-aminobenzoate). However, this document discloses to produce the p-aminobenzoic acid in either *E. coli* or in *S. cerevisiae* and fails to recognize the advantages of *Corynebacterium glutamicum* as a host. In addition, this document does also not disclose how to successfully combine the fermentation process with the downstream chemical process of converting the biologically-derived p-aminobenzoic acid to aromatic amines, e.g. aniline. Regarding the downstream chemical process technology of how to convert chemically or biologically produced the p-aminobenzoic acid this document merely refers to distillation methods without recognizing the advantageous technical benefits of combining this part with the upstream part of providing the p-aminobenzoic acid in form of a continuous process.

A direct fermentation of sugar to aniline as a one-step conversion was thought to be most cost efficient if based on a biosynthesis pathway including an enzymatic, in vivo, decarboxylation of anthranilate to aniline as the final reaction step. Since an aminobenzoate decarboxylase could not successfully be identified or developed through protein engineering, the decarboxylation reaction of anthranilate to aniline could not be carried out by pure enzymatic means. Since such a one-step process was not technically feasible, process alternatives to perform the final reaction step of decarboxylating anthranilate to aniline as the final reaction step were taken into consideration, e.g. by a chemical step, as opposed to an enzymatic step.

SUMMARY

Therefore, it has been the technical problem of the invention to provide a method of producing aniline that is either based on chemical starting products or that is based on renewable resources that is superior to existing chemical and fermentation methods and that achieves a large reduction in carbon dioxide emissions, independence from fossil resources, and similar or lower production cost compared to the established petroleum-based production processes.

The invention has further solved said problem by providing a method for producing aniline, comprising the steps of:
a) providing o-aminobenzoate, wherein said o-aminobenzoate comprises anthranilate anion and a suitable cation,
b) converting said anthranilate anion to aniline by thermal decarboxylation in the presence or absence of a catalyst,
c) extracting the aniline produced in step b) in an organic solvent at least once, and
d) purifying the aniline produced in steps b) and c) by distillation, wherein said distillation produces aniline and a water phase.

The change to aniline production based on renewable resources, e.g. biomass or fermentable carbon sources, offers the advantages of reducing $CO_2$ emissions significantly, allows for independence from fossil resources, and enables a possible reduction in production cost. A further advantage of the invention is that the use of hazardous chemicals and the resulting waste are kept to a minimum. Further, biologically derived o-aminobenzoate can be produced and converted to aniline in a process with much less overall impact on the environment.

DETAILED DESCRIPTION

Figure 1:
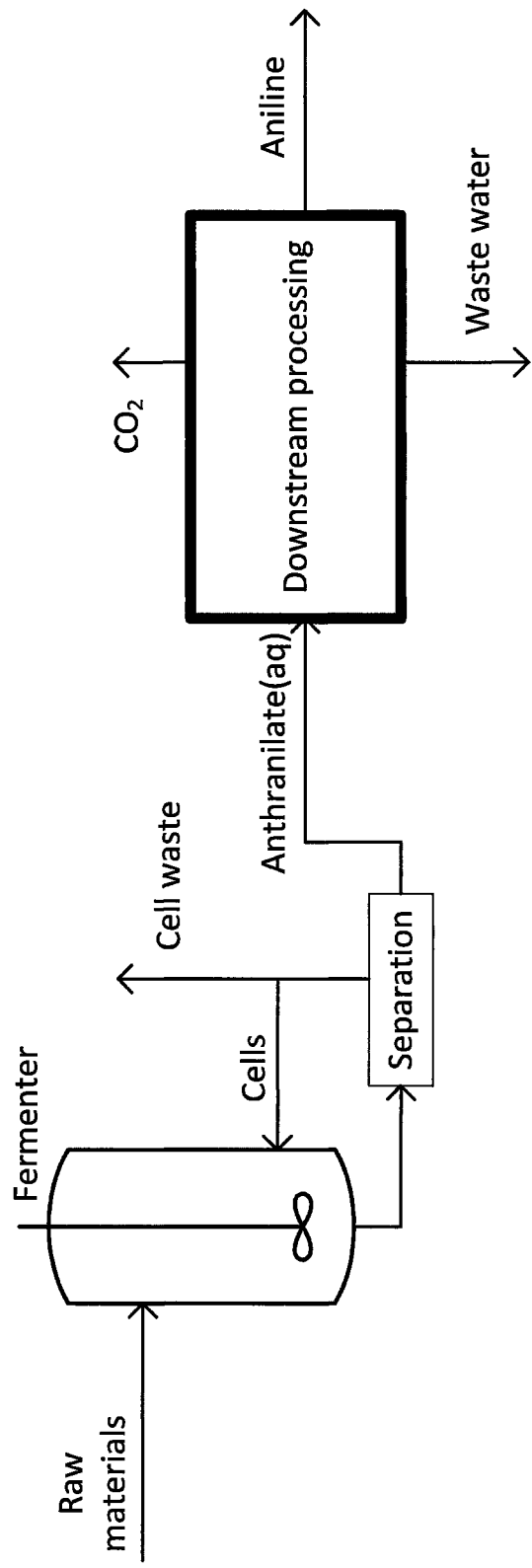
FIG. 1 shows the overall concept of the method according to the invention comprising the conversion of raw materials to anthranilate in the fermentation step followed by a chemical conversion and purification to aniline in the downstream processing.

In the following, a few terms used to describe the invention are defined.

The term "bioaniline" according to the invention refers to aniline that is based on raw material from renewable resources, such as sugar beet, sugar cane, starch-containing plants, preferably corn, wheat and rye, and lignocellulose, preferably straw, wood and bagasse, glycerol and C1-compounds, preferably CO, or such as fermentable sugars, preferably C-5 monosaccharides, C-6 monosaccharides, disaccharides, and tri-saccharides, wherein the C-5 monosaccharides preferably are xylose and arabinose, and wherein the C-6 monosaccharides preferably are glucose, fructose or mannose, and wherein the disaccharide preferably is saccharose, and wherein the trisaccharide preferably is kestose.

"o-aminobenzoate" according to the invention refers to ortho-aminobenzoate (o-aminobenzoate, "oAB", "2-AB"). o-aminobenzoate can be present in the form of the anthranilate salt comprising the anthranilate anion, $C_6H_4COO^-$, and a suitable cation, such as $NH4^+$ or $Na^+$, or as anthranilic acid, which is the zwitter ion $C_6H_4COO^-$ $NH_3^+$ and $C_6H_4COO^-$ $NH_2$. "o-aminobenzoate" ("oAB", "2-AB") is different from "4-aminobenzoate" ("para-AB", "p-AB") in that the amino group is attached to the benzene ring at the $C_4$-position (para) as opposed to the $C_2$-position (ortho) in the case of o-aminobenzoate ("oAB"). "o-aminobenzoate" according to the invention can either be provided by conventional chemical methods or as a chemical that is commercially obtained, or it can be provided biologically by means of a recombinant microbial host that is capable of producing o-aminobenzoate by fermentation. One example for a chemical, commercially obtained o-aminobenzoate is oAB as purchased from Sigma Aldrich, catalog no. A89855.

The term "host" within the meaning of the invention can comprise any host that is capable of producing o-aminobenzoate by fermentation, either naturally, or only after transformation as a "recombinant microbial host", or in addition to the naturally present o-aminobenzoate, either in the form of the anthranilate anion or as anthranilic acid, following transformation. A "microbial host" according to the invention can be selected from the group consisting of bacteria, yeast and fungi. Said host can be selected from the group consisting of bacteria, yeast and fungi, wherein said bacterium preferably is an *Escherichia coli* strain, a *Corynebacterium* strain or a *Pseudomonas* strain, wherein said *Corynebacterium* strain preferably is *Corynebacterium glutamicum* and wherein said *Pseudomonas* strain preferably is *Pseudomonas putida*. Preferably, said microbial host can be a recombinant microbial host. Such a recombinant microbial host can be *E. coli* W3110 trpD9923, as shown in Example 1, or it can be *Corynebacterium glutamicum* ATCC 13032or it can also be *Pseudomonas putida* KT2440.

The term "genetic modification" within the meaning of the invention refers to changes in nucleic acid sequence of a given gene of a microbial host as compared to the wild-type sequence. Such a genetic modification can comprise deletions as well as insertions of one or more deoxyribo nucleic acids. Such a genetic modification can comprise partial or complete deletions as well as insertions introduced by transformations into the genome of a microbial host. Such a genetic modification can produce a recombinant microbial host, wherein said genetic modification can comprise changes of at least one, two, three, four or more single nucleotides as compared to the wild type sequence of the respective microbial host. For example, a genetic modification can be a deletion or insertion of at least one, two, three, four or more single nucleotides or a transformation of at least one, two, three, four or more single nucleotides. A genetic modification according to the invention can have the effect of e.g. a reduced expression of the respective gene or of e.g. an enhanced expression of the respective gene. In one example of such a genetic modification according to the invention, a recombinant microbial host, e.g. *Escherichia coli*, can comprises a genetic modification of the trpD gene encoding the enzyme anthranilate phosphoribosyl transferase, wherein said genetic modification can have the effect of a reduced expression of the modified trpD gene. Such a recombinant microbial host comprising can be *E. coli* W3110 trpD9923, as shown in Example 1.

The term "batch fermentation" within the meaning of the invention refers to a single fermentation reaction having a defined starting point and a defined end point. Batch fermentation can be used in step a) of the method according to the invention in cases where the production rates of the microorganisms cannot be maintained at a high rate in continuous fermentation mode.

The term "fed-batch fermentation" within the meaning of the invention is defined as an operational technique in biotechnological processes where one or more nutrients (substrates) are fed (supplied) to the bioreactor during cultivation and in which the product(s) remain in the bioreactor until the end of the run. "Fed-batch fermentation" can be used in step a) of the method according to the invention in cases where the production rates of the microorganisms cannot be maintained at a high rate in continuous fermentation mode.

The term "continuous fermentation" within the meaning of the invention, refers to a fermentation method in which substrate is added and the product (i.e. o-aminobenzoate, oAB) is removed continuously during the fermentation in step a) of the method according to the invention.

In the following, the invention is described in more detail.

The invention provides a method for producing aniline, comprising the steps of:
a) providing o-aminobenzoate, wherein said o-aminobenzoate comprises anthranilate anion and a suitable cation,
b) converting said anthranilate anion to aniline by thermal decarboxylation in the presence or absence of a catalyst,
c) extracting the aniline produced in step b) in an organic solvent at least once, and
d) purifying the aniline produced in steps b) and c) by distillation, wherein said distillation produces aniline and a water phase.

In a preferred embodiment of the method according to the invention, the o-aminobenzoate in step a) of providing o-aminobenzoate is provided chemically or produced biologically, preferably it is produced biologically by fermentation of a raw material comprising at least one fermentable carbon substrate using a recombinant microbial host cell capable of converting said raw material comprising a fermentable carbon substrate to o-aminobenzoate by fermentation, wherein said o-aminobenzoate comprises anthranilate anion and a suitable cation. Such a suitable cation of step a) can be $NH^{4+}$ or $Na^+$, as comprised e.g. in $NH_4OH$ solution and in NaCl solution.

In a further embodiment of the method according to invention, the fermentation of step a) of producing o-aminobenzoate can be a batch fermentation, a fed-batch fermentation or a continuous fermentation. Such a fermentation can be performed in a fermentation reactor, in which a recombinant microbial host cell capable of converting the raw material comprising a fermentable carbon substrate to o-aminobenzoate by fermentation is cultivated. Such cultivation can be carried out in the presence of a suitable carbon source, for example corn syrup, sugar can juice, molasses and the like. Such cultivation can also be carried out in the presence of a suitable nitrogen source, for example ammonia gas, ammonium hydroxide solution, ammonium sulfate, ammonium nitrate, corn steep liquor and the like in the presence of micro-nutrients needed for survival of the recombinant microbial host cell. The pH in such a fermentation can be kept at a value between 6.5 and 7.5 with addition of a base for example, ammonia gas, ammonium hydroxide, sodium hydroxide, and the like.

Producing the o-aminobenzoate biologically in step a) of the method of the invention can be performed by continuous fermentation, preferably in a fermenter that is operated continuously. In such a continuous fermentation according to the invention, fermentation broth is being withdrawn continuously from the fermenter and processed through a device to separate the biomass, for example by filtration, a centrifuge, membranes, and the like.

Sufficient oxygen can be added to the fermentation reactor used in step a), either pure, as air, or as enriched air. The cell free fermentation broth is essentially a solution of an o-aminobenzoate (oAB) salt with the anthranilate anion and a counter cation. The oAB solution can have a concentration between 5 g/litre and 500 g/litre, preferably between 20 g/litre and 200 g/litre, and most preferably between 50 g/litre and 150 g/litre of oAB salt.

In a preferred embodiment of the method according to the invention, step a) through to step d) can be run continuously.

The suitable cation of step a) of producing o-aminobenzoate can be $NH^4$ or Nat In a particularly preferred embodiment of the method according to the invention the recombinant microbial host of step a) of producing o-aminobenzoate can be removed prior to the subsequent conversion of said anthranilate anion to aniline by thermal decarboxylation in step b). Such removed recombinant microbial host can preferably be re-fed to the fermentation of step a) of producing o-aminobenzoate. That means that the biomass comprising the recombinant microbial host can be recycled to the fermenter and fermentation of step a) after purging a small portion the biomass comprising the recombinant microbial host. Such purge stream from the biomass can be useful in order to avoid biomass accumulation. A portion microbial host cell that multiply in the fermenter and the dead cells can thus be removed in order to keep the concentration of live host cells in the reactor of fermentation step a) within defined limits, most preferably constant. This can be different in the case of fed-batch fermentation, where the recombinant host cells and the fermentation product(s) remain in the bioreactor until the end of the run, which therefore is not a continuous fermentation but a fed-batch fermentation.

When performing the conversion of said anthranilate anion to aniline by thermal decarboxylation in the presence or absence of a catalyst in step b) of the method according to the invention, the catalyst, if used, can be a heterogeneous acid catalyst, preferably a zeolite, most preferably zeolite H-Y, zeolite H-Y (GO257), e.g. as obtained from Zeolyst International, catalog no. CBV600. The acid catalyst zeolite H—Y (GO257, $SiO_2/Al_2O_3$=5.5) has a particularly high acidic character and has a wider pore size (0.7-0.8 nm) than e.g. ZSMS-27, which also possesses acidic character, but which has smaller pore size (0.5 nm) so that AA molecules cannot penetrate into them and consequently do not have access to the active sites of the acidic catalyst.

In a further embodiment, when performing the converting of said anthranilate anion to aniline by thermal decarboxylation in the presence or absence of a catalyst in step b) of the method according to the invention, the catalyst, if used, can also be a heterogeneous base catalyst, preferably a layered double hydroxide, most preferably Mg—Al hydrotalcite, which has a basic character (HTC, $Mg_6Al_2(CO_3)(OH)_{16}.4H_2O$).

When performing the thermal decarboxylation of step b) of the method according to the invention the o-aminobenzoate solution of step a) comprising anthranilate anion and a suitable cation can be fed to a chemical reactor that can operate at a temperature between 150° C. and 250° C., preferably between 160° C. and 220 ° C., most preferably between 180° C. and 200° C.

The reaction time for performing the thermal decarboxylation of step b) of the method according to the invention should be sufficient for a reaction to aniline with a high yield. More specifically, the time requirement for performing the thermal decarboxylation of step a) can be in the order of 0.5 hours to 3 hours The pressure in the reactor, wherein the thermal decarboxylation step b) can be performed, can be selected as a function of how much of the water and aniline is allowed to evaporate during the reaction and to leave the reactor with the $CO_2$ produced during the thermal decarboxylation reaction. The product of the thermal decarboxylation step b), i.e. the reactor effluent, can essentially be a homogenous water aniline mixture.

This reactor effluent of step b) may be fed directly to a heteroazeotropic distillation sequence, in which water and aniline are recovered as bottom products. This option can be performed if following the thermal decarboxylation of step b) has a high content of aniline, usually if above 120 g/liter. However, for a low concentration of aniline following the thermal decarboxylation step b), e.g. 120 g/liter and less, direct aniline separation following step b) is practically infeasible by distillation alone, since the energy consumption becomes prohibitively large.

Therefore, the method according to the invention comprises the further step c) of extracting the aniline produced in the thermal decarboxylation of step b) in an organic solvent at least once, in advance of proceeding to step d) of purifying the aniline by distillation. In this way, the extraction step c) is used as a pre-concentration step in advance of distillation in step d). The aniline water mixture that is the product of the thermal decarboxylation of step b) can fed to an extraction device, e.g. a mixer settler, a pulse column, and the like, where it can contact a nonpolar organic solvent with a high affinity for aniline, preferably one with a higher boiling point than that of aniline, for example 1-dodecanol. The organic solvent that is used in the method according to the invention can be selected from the group consisting of alcohols, phenols, amides, ethers and aromatic hydrocarbons. In a preferred embodiment of the invention, the alcohol used as the organic solvent preferably is 1-dodecanol.

In a further embodiment of the method according to the invention, the extraction of aniline in an organic solvent in step c) can be performed for more than one time for a further pre-concentration of aniline in advance of distillation in order to obtain an even higher yield of aniline produced.

The organic solvent used in the extraction of step c) can preferably be recovered. Such a recovering of organic solvent can preferably be done by distillation. The recovered organic solvent can preferably be re-fed to step c) of the method to be re-used again for extracting the aniline produced in step b). That means that the aniline-organic solvent mixture can be distilled, wherein aniline and any water entrained or dissolved in it and the nonpolar solvent can be recovered as an overhead product. The overhead stream that contains aniline at a concentration ranging is then fed to the distillation of step d), which can be a heteroazeotropic distillation.

In yet another embodiment of the method according to the invention, the method comprises a further step e) of re-feeding the water-phase of the extraction performed in step c) to the fermentation of step a).

The method can also comprise the additional step of re-feeding the water-phase of the distillation performed in step d) to the fermentation of step a).

The $NH_4^+$ cation that can be used as a suitable cation in the production step a) of the method according to the invention can be recovered as $NH_3$ subsequent to the distillation of step d) and re-fed to the fermentation of step a).

When the production step a) of the method according to the invention comprises fermentation, the raw material to be used in the fermentation of step a) can be selected from the group consisting of sugar beet, sugar cane, starch-containing plants, preferably corn, wheat and rye, and lignocellulose, preferably straw, wood and bagasse, glycerol and C1-compounds, preferably CO.

When the production step a) of the method according to the invention comprises fermentation, the at least one fermentable carbon substrate comprised in the raw material to be used in the fermentation of step a) can be selected from the group consisting of C-5 monosaccharides, C-6 monosaccharides, disaccharides, and tri-saccharides, wherein the C-5 monosaccharides preferably are xylose and arabinose, and wherein the C-6 monosaccharides preferably are glucose, fructose or mannose, and wherein the disaccharide preferably is saccharose, and wherein the trisaccharide can preferably be kestose.

The recombinant microbial host that can be used in the fermentation step a) of producing o-aminobenzoate can be selected from the group consisting of bacteria, yeast and fungi, wherein said bacterium preferably can be an *Escherichia coli* strain, a *Corynebacterium* strain or a *Pseudomonas* strain, wherein said *Corynebacterium* strain preferably can be *Corynebacterium glutamicum* and wherein said *Pseudomonas* strain preferably can be *Pseudomonas putida*.

In a preferred embodiment of the invention, the recombinant microbial host that can be used in the fermentation of step a) can be *Escherichia coli*, preferably *E. coli* W3110, even more preferably *E. coli* W3110 trpD9923 (purchased from the *E. coli* Genetic Resource Center at Yale University).

In a preferred embodiment of the invention, the recombinant microbial host that can be used in the fermentation of step a) can be *Corynebacterium glutamicum* ATCC 13032, or a further recombinant microbial host that is based on this strain.

In a preferred embodiment of the invention, the recombinant microbial host that can be used in the fermentation of step a) can be *Pseudomonas putida* KT2440, or a further recombinant microbial host that is based on this strain.

The invention further provides the use of the aniline produced according to the method of the invention as described herein and as claimed in the claims for producing methylenedianiline (MDA), wherein the aniline produced is further converted to methylenedianiline (MDA) with formaldehyde in the presence of water and catalyst. The MDA produced can be further converted to methylenediisocyanate (MDI) with phosgene.

It will be apparent to those skilled in the art that various modifications can be made to the methods and recombinant host strains of the invention. Thus, it is intended that the present invention covers such modifications and variations, provided they come within the scope of the appended claims and their equivalents.

FIGURES AND TABLES

FIG. 1 shows the overall concept of the method according to the invention comprising the conversion of raw materials to anthranilate in the fermentation step followed by a chemical conversion and purification to aniline in the downstream processing.

Figure 2:
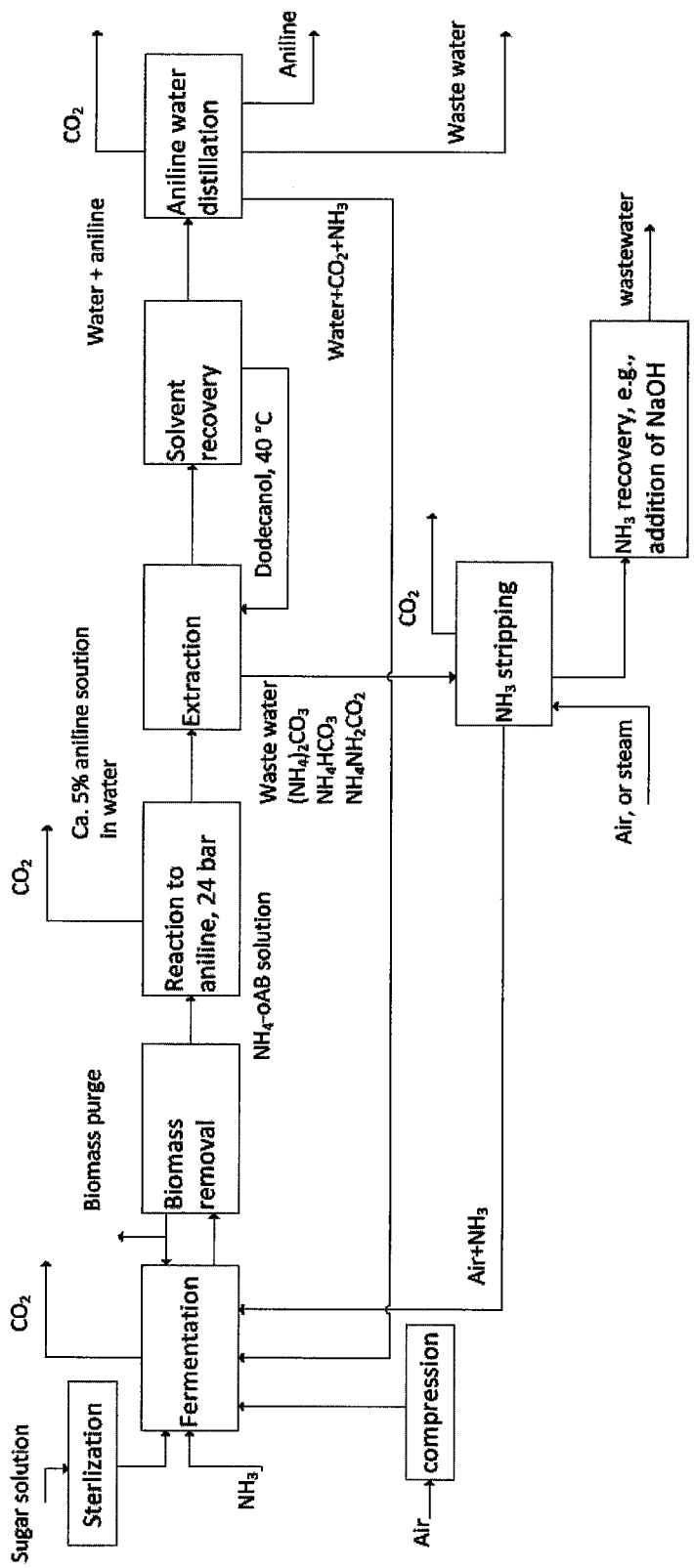
FIG. 2 shows a more detailed overview of the method according to the invention. The suitable cation of step a) can be $NH_4^+$ or $Na^+$, so $NH_3$ or NaOH can be used as a buffer in the fermenter.

FIG. 2 shows a more detailed overview of the method according to the invention. The suitable cation of step a) can be $NH_4^+$ or $Na^+$, so $NH_3$ or NaOH can be used as a buffer in the fermenter.

Figure 3:
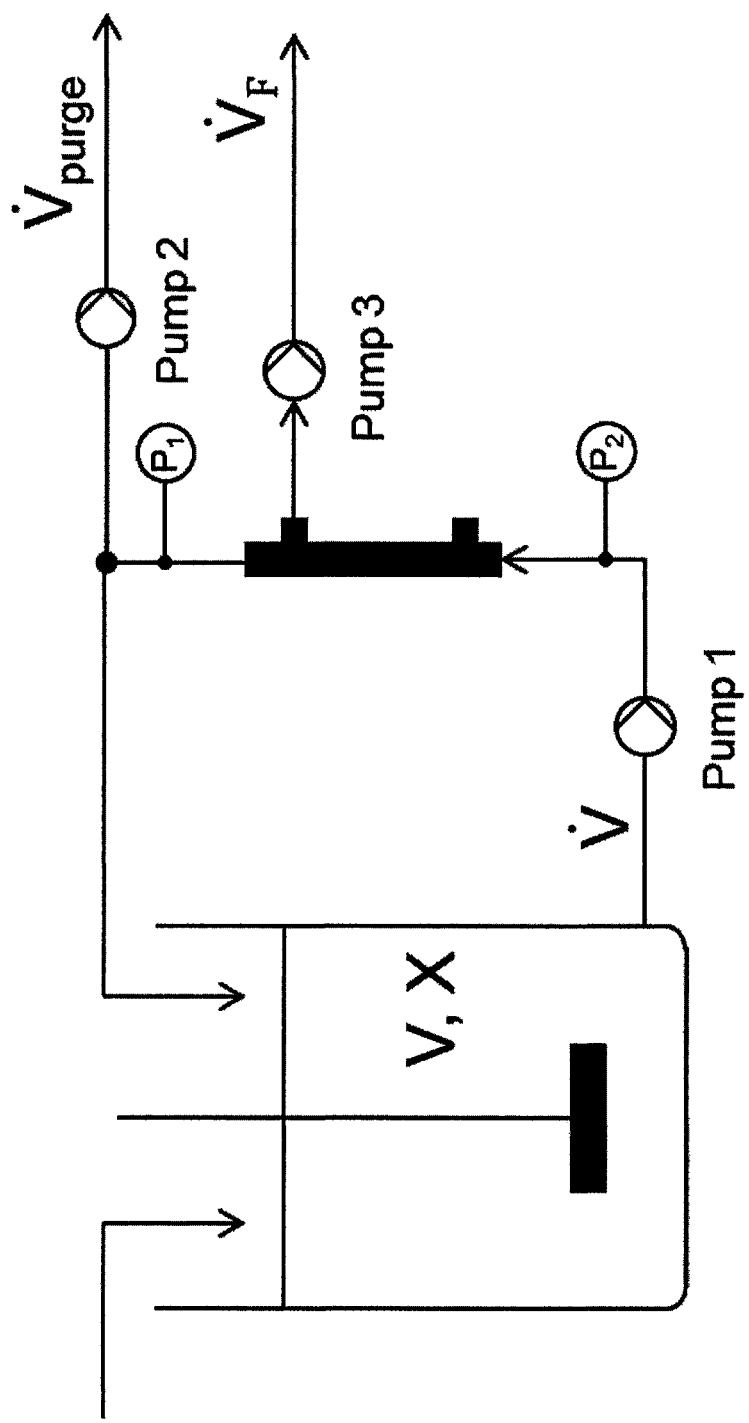
FIG. 3 shows the integration of a hollow fiber filtration module with a cut of value of 750 kDa for cell retention during continuous fermentation.

FIG. 3 shows the integration of a hollow fiber filtration module with a cut of value of 750 kDa for cell retention during continuous fermentation.

Figure 4:
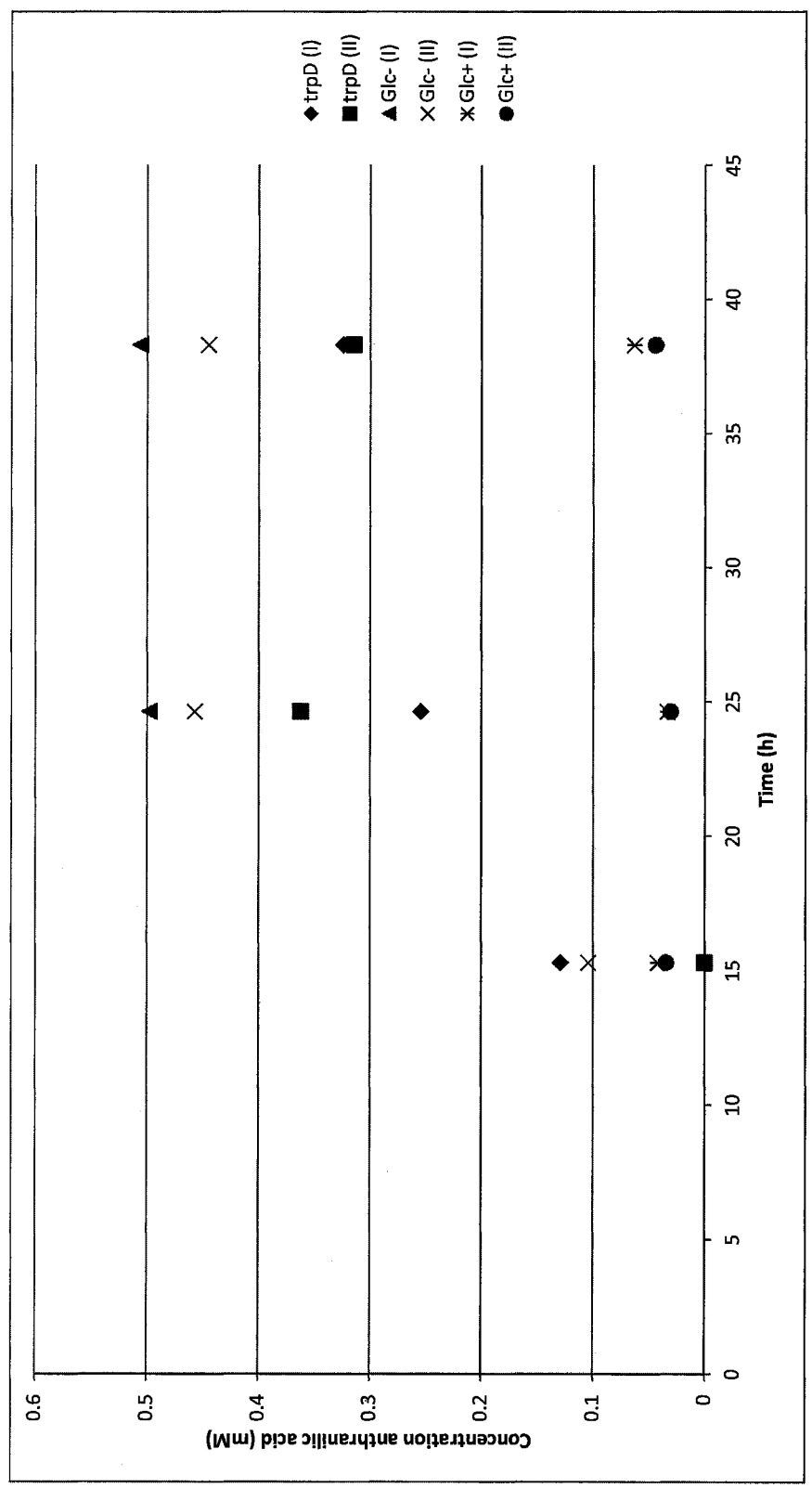
FIG. 4 shows anthranilic acid production in the strains *E. coli* W3110 trpΔ9923 Δpts Glc+ (with 0.51 mM, best results), followed by *E. coli* W3110 trpΔ9923 (with nearly 0.2 mM less than Glc+ after 38 h) and the lowest production rate was with *E. coli* W3110 trpΔ9923 Δpts Glc− (with 5× less concentration of produced anthranilic acid after 38 h).

FIG. 4 shows anthranilic acid production in the strains *E. coli* W3110 trpΔ9923 Δpts Glc+ (with 0.51 mM, best results), followed by *E. coli* W3110 trpΔ9923 (with nearly 0.2 mM less than Glc+ after 38 h) and the lowest production rate was with *E. coli* W3110 trp49923 Δpts Glc− (with 5× less concentration of produced anthranilic acid after 38 h).

Figure 5:
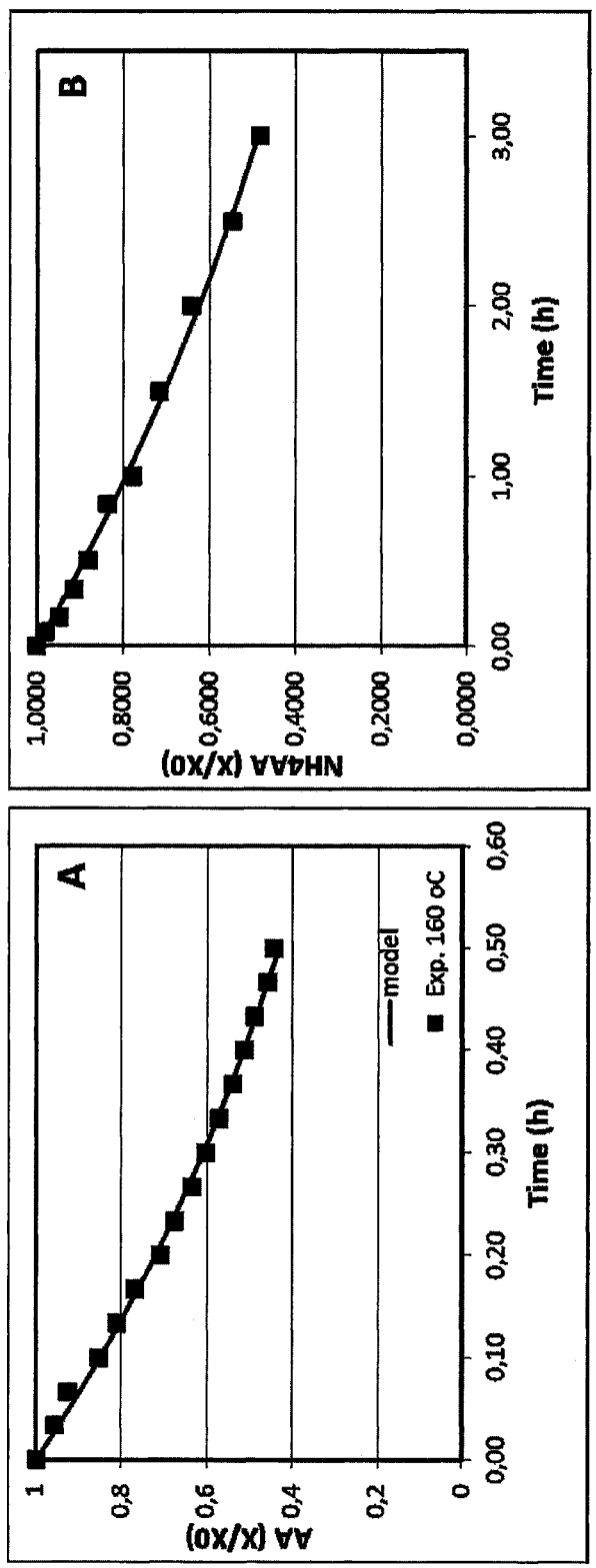
FIG. 5 shows the kinetics of decarboxylation of A) AA 0.5 wt % and of B) $NH_4AA$ 3 wt % in aqueous buffer solution at 160° C.

FIG. 5 shows the kinetics of decarboxylation of A) AA 0.5 wt % and of B) $NH_4AA$ 3 wt % in aqueous buffer solution at 160° C.

Figure 6:
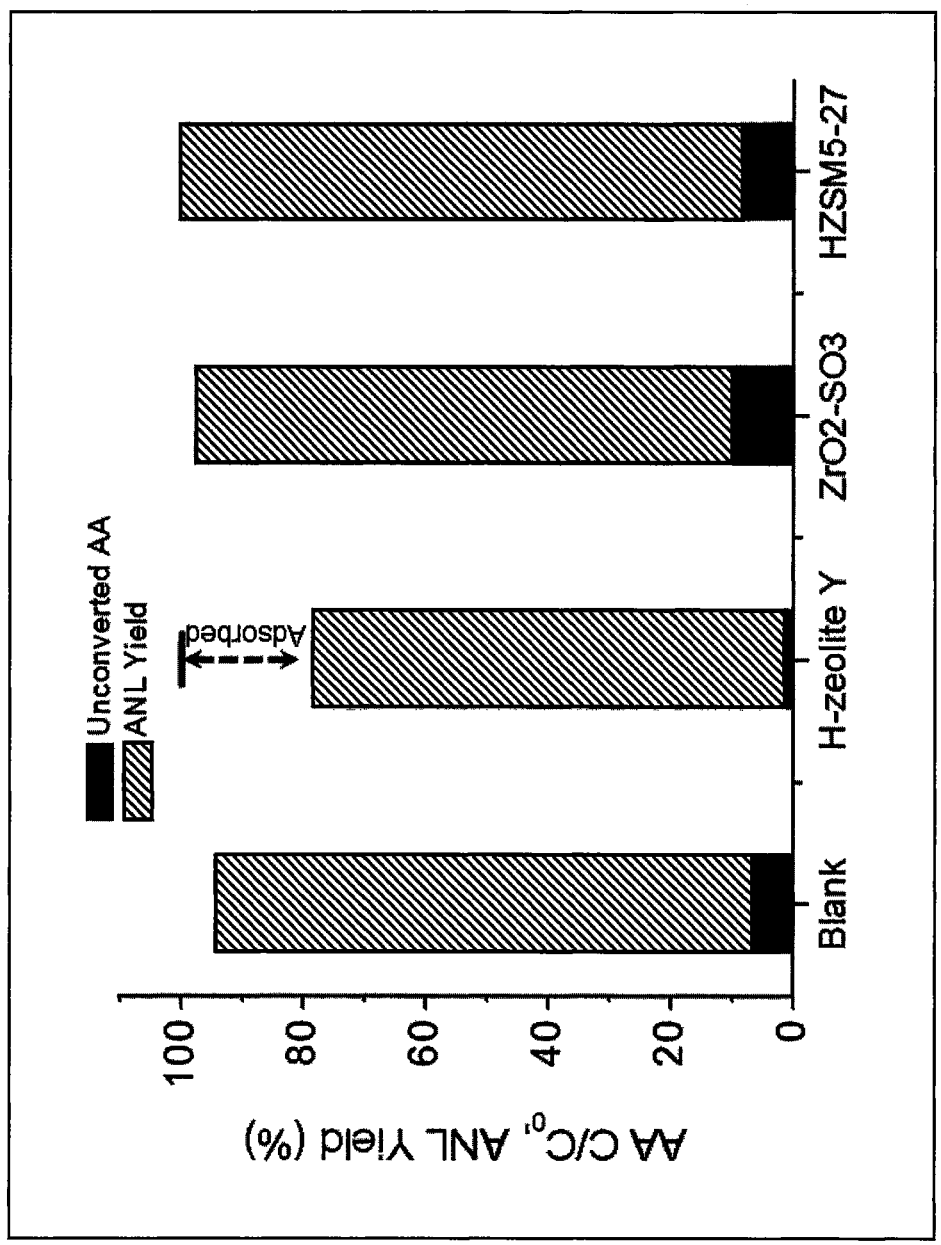
FIG. 6 shows the kinetics of decarboxylation of $NH_4AA$ with different catalysts, i.e. Zeolite H—Y, Zeolite H-ZSMS and Sulphated Zirconia, as described in Example 3.

FIG. 6 shows the kinetics of decarboxylation of $NH_4AA$ with different catalysts, i.e. Zeolite H-Y, Zeolite H-ZSMS and Sulphated Zirconia, as described in Example 3.

Table 1 shows the orders of reaction and rate coefficients of decarboxylation of anthranilic acid (AA) and NH$_4$AA in buffer solutions at 160° C. and 180° C. shown in Example 2.

Table 2 shows a comparison of the absorption capacities of metal-exchanged zeolite Y with ZSM-5 and Hydroxyapatite, as shown in Example 4.

EXAMPLES

Example 1

Experiments to Produce Anthranilic Acid with *E. coli*

The strain *E. coli* W3110 trpD9923 was purchased from the *E. coli* Genetic Resource Center at Yale University. The strain had been created by random mutagenesis and contained a mutated trpD gene called trpD9923. The related truncated enzyme of the trpD9923 gene had lost its ability to catalyze the reaction of anthranilate phosphoribosyl transferase, but had maintained its anthranilate synthase activity. The strain can therefore synthesize anthranilate, but cannot metabolize it further to tryptophan and is thus tryptophan auxotroph. This leads to an overflow of anthranilate.

This strain was grown in 50 ml shake flasks with a 10 ml culture volume at 28° C. and 140 rpm. The medium used was the mineral medium M9 with tryptophan defined as follows: 10 g/l glucose, 6 g/l Na2HPO4, 0.5 g/l NaCl, 3 g/l KH2PO4, 1 g/l NH$_4$Cl, 246.5 mg/l MgSO$_4$, 14.7 mg/l CaCl$_2$, 10 mg/l Thiamin (vitamin B1), 20 mg/l tryptophan. The strain produced 60 mg/l anthranilic acid after 25.5 h as measured by HPLC. The strains compared were *E. coli* W3110 trpΔ9923; *E. coli* W3110 trpΔ9923 Δpts Glc+; and *E. coli* W3110 trpΔ9923 Δpts Glc−. The tryptophan auxotrophy was confirmed in the trpD9923 strain. Fermentation with mineral medium M9 containing tryptophan the strain produced 60 mg/L anthranilic acid.

The strain was further optimized by inactivating the phosphotransferase system using knock out deletion. The pts deficient strain was adapted to growth on glucose and tested for anthranilate production using a 25 ml shake flask fermentation at 37° C. and 150 rpm with a culture volume of 10 ml. The same medium as for the pts positive strain was used. It produced 69 mg/L after 25 hours as measured by HPLC. Production of anthranilic acid by the three strains *E. coli* W3110 trpΔ9923; *E. coli* W3110 trpΔ9923 Δpts Glc+; and *E. coli* W3110 trpΔ9923 Δpts Glc− saw a significant improvement after a previous incubation in LB medium. The best anthranilic acid production strain was *E. coli* W3110 trpΔ9923 Δpts Glc+ (with 0.51 mM), followed by *E. coli* W3110 trpΔ9923 (with nearly 0.2 mM less than Glc+ after 38 h) and the worst one was *E. coli* W3110 trpΔ9923 Δpts Glc− (with 5× less concentration of produced anthranilic acid after 38 h), as can be seen in FIG. 4.

Example 2

Kinetics of Decarboxylation of A) AA 0.5 wt % and of B) NUM without Catalyst

In this experiment, the kinetics of the thermal decarboxylation of step b) of the method according to the invention was studied. If NH$_4$OH solution was added to the anthranilic acid (AA) buffer solution, AA was gradually transformed to ammonium anthranilate, which had a much higher solubility (up to 10%) than AA itself. In this case it was possible to decarboxylate anthranilate ion to aniline (ANL). AA, or o-aminobenzoate, respectively was either provided biologically by a recombinant microbial host as described in Example 1, or it was provided chemically, e.g. it was commercially obtained, e.g. from Sigma Aldrich, catalog no. A89855.

A buffer solution containing (NH$_4$)$_2$SO$_4$ (20 g/L), Na$_2$HPO$_4$ (1 g/L) and KH$_2$PO$_4$ (1 g/L) in distilled water was prepared. Then AA 10 wt % was suspended in this solution. NH$_4$OH solution (28-30% NH$_3$) was added dropwise into this suspension until a clear yellow solution was formed. The pH of this ammonium anthranilate (NH$_4$AA) solution was around 7. The ammonium anthranilate (3 wt %) solution was also prepared using this method.

80 mL of each of the above solutions was transferred into an autoclave 160 mL and heated to 160° C. or 180° C. and samples were taken at different time intervals to analyse the rate of aniline (ANL) formation.

Decarboxylation of AA 0.5 wt % and NH$_4$AA 3 wt % in aqueous buffer solution was performed at 160° C. without using any catalyst. The studies using a model resulted in pseudo-first order kinetics for both reactions. The profiles of these reactions are shown in FIG. 5. The kinetic model was established using the general reaction rate formula as below and considering the experimental data to calculate the optimized k and n parameters which are the rate coefficient and the order of reaction, respectively.

$$r = \frac{d[A]}{dt} = k[A]^n$$

$$d[A] = k[A]^n \times dt$$

$$[A]_{t+\Delta t} = [A]_t - k([A]_t)^n \times \Delta t$$

As presented in Table 1 below, the orders (n) of these reactions are close to 1. The rate coefficient (k) of AA 0.5 wt % decarboxylation in water is 6.8 times bigger than that of NH4AA 3 wt %.

The kinetics of NH4AA 10 wt % decarboxylation at 160° C. and 180° C. was also studied using experimental data and a simulating model.

TABLE 1

Orders of reaction and rate coefficients of decarboxylation of AA and NH$_4$AA in buffer solutions at 160° C. and 180° C.

| Reactant | Reaction temperature (° C.) | n | k (h$^{-1}$) |
|---|---|---|---|
| AA 0.5% in buffer solution | 160 | 0.9207 | 0.0519 |
| NH$_4$AA 3% in buffer solution | 160 | 0.8706 | 0.00755 |
| NH$_4$AA 10% in buffer solution | 160 | 1.2758 | 0.000713 |
| NH$_4$AA 10% in buffer solution | 180 | 0.9793 | 0.026 |

As it is observed (Table 1 and FIG. 5), both reactions followed pseudo-first order kinetics. In addition, the rate coefficient of the reaction at 180° C. is 36 times bigger than that at 160° C. This number is very competitive with that of the AA 0.5 wt % decarboxylation in water. Most importantly, there is a great advantage of 20 times higher concentration in case of NH4AA. Example 2 shows that oAB salts can be decarboxylated in aqueous solutions with a reaction following first order kinetics. Thus virtually complete conversion of anthtranilate ion to aniline can be achieved, e.g. in a plug flow reactor or in a cascade of mixed tanks.

Example 3

Kinetics of Decarboxylation of NH₄AA with a Catalyst

This example follows the same procedure as Example 2, except that to the 80 mL of solution 1.6 g (2%) of acidic catalyst were added. The catalysts employed were Zeolite H-Y (Zeolyst International, catalog no. CBV600), Zeolite H-ZSMS (Süd-Chemie/Clariant catalog no. H-MFI-27) and Sulphated Zirconia (Mel Chemicals catalog no. MELCat) (ZO 1720). In FIG. 6 the results are compared with the experiment without catalyst (Blank) as described in Example 2. The blank experiment, sulfated zirconia and ZSM-5 all three reached a comparable conversion of AA of 90-92%. Only the catalyst ZSM-5 showed a higher conversion of AA to aniline, i.e. up to 99%.

Example 4

Adsorption/Desorption of Anthranilic Acid on Mineral Absorbers

As can be seen from Example 3 and FIG. 6, the zeolite-Y catalyst, even with the highest catalytic activity and conversion, with almost no anthranilic acid left, was not giving the highest yield of aniline as product. Analysis of the solid revealed that the missing part of the aniline product was strongly absorbed on the catalyst itself.

The adsorption capacity of AA on different types of adsorbents was tested. Zeolite Y (Zeolyst International, catalog no. CBV600) and ZSMS (Sued-Chemie/Clariant catalog no. H-MFI-27) were selected as zeolites, which function as molecular sieves for different molecules. Hydroxyapatite ($Ca_{10}(PO_4)_6(OH)_2$) (Sigma-Aldrich catalog no. 289396) was tested due to its ability in the adsorption of AA and some other similar compounds in different solvents.

Adsorption test: Adsorbents were already calcined at 300° C. for 3 h to release any remained moisture. A solution of AA (0.5 wt %) in water was prepared. 20 mL of this solution was transferred to a 50 mL flask containing 0.2 g adsorbent. After a certain period of time under stirring, the concentration of AA in water was analysed by HPLC. The decrease of AA concentration in water was considered as the adsorbed AA.

Synthesis of metal-exchanged zeolite: given the improved adsorption capacity of Ca-incorporated zeolite, Ca-exchanged zeolites were prepared by ion exchange to be tested in the adsorption of AA. 3 g zeolite H-Y as powder was added to a solution of $Ca(NO_3)_2 \cdot 4H_2O$ (0.5 M). The slurry was stirred for 4 h and then the solution was replaced by a fresh one and this procedure was repeated two more times. Finally, the solids were separated by centrifuge and dried at 80° C. and calcined at 300° C. for 3 h. Four other metal-exchanged zeolite Y samples using K, Na, Mg and Fe were prepared with the same method as described above. The samples were then labelled K—Y, Na—Y, Ca—Y, Mg—Y and Fe—Y.

The results of the absorption study are summarized in Table 2 below:

TABLE 2

Comparison of absorption capacities of metal-exchanged zeolite Y with ZSM-5 and Hydroxyapatite

| Absorbent | HAP | H-ZSM5 | H-Y | Na-Y | K-Y | Mg-Y | Ca-Y | Fe-Y |
|---|---|---|---|---|---|---|---|---|
| Absorption capacity (gAA/kg absorbent) | 10.8 g/kg | 11.6 g/kg | 24.8 g/kg | 25.0 g/kg | 27.4 g/kg | 27.6 g/kg | 36.8 g/kg | 51.2 g/kg |

The absorption capacity of Zeolite Y is superior as compared to ZSM-5 and Hydroxyapatite. This was probably due to the larger pore size and different pore structure. This could also be increased further by exchange with cations. The trend with charge and size of the cation was evident, so the absorption process was strongly dependent from the surface charge of the absorber.

By contacting the loaded absorber with 80 ml of 10% NaOH water, it was possible to extract the absorbed AA back into the solution, with a yield of up to 80%. By contacting it with 80 ml of buffer solution at pH 7, i.e. the same used for the absorption process, almost no desorption (<10%) was observed. This example shows that the absorption process is a thermodynamically equilibrated system which is dependent from surface charge.

Example 5

Solvent Selection for Extraction and Aniline Distribution Coefficient Between Water Phase and Solvent (Organic) Phase A solvent screening on the basis of COSMO calculations was done. The COSMO method was employed having the following two steps:
  a) determination of the surface charges on the molecules surrounded by a good conducting medium with quantum chemical calculations.
  b) deriving from the charge distribution the chemical potential of the solute in various solvents.

In addition, the following further restrictions had to be taken into account: low solubility in water, moderate viscosities, density and interfacial tension enable a comfortable phase separation, high boiler relative to aniline. As a result long chain alcohols and long chain amines and mixtures of both have been found (7<C–number<17).

Unifac Calculations for two alcohols are shown below in Table 3.

TABLE 3

| component | conc. of solvent in the water phase [wt %] | conc. of water in the organic phase [wt %] |
|---|---|---|
| 1-decanol | 0.018 | 1.46 |
| 1-dodecanol | 0.0026 | 0.19 |

Using a mixture of dodecanol isomers can offer the advantage of low mutual solubility and a lower melting point.

Example 6

Design Calculations for Extraction of Aniline from Water

The feed stream composition in this example was 93% water, 7% aniline. The column used was a pulsed column.

The packing was done by metal structured packing (due to high throughput) with a specific surface of 500 (examples of packing: Mellapack 500Y or Montz B1-500). The material was stainless steel.

The dimensions were as follows: for a capacity of 60 t/h of aqueous feed (dodecanol flow rate calculated using F/S=2 wt/wt):
Column inner active diameter=1200-1300 mm
Active packing length=11-12 m
Total column length=14-15 m
For a capacity of 200 t/h (dodecanol flow rate calculated using F/S=2 wt/wt):
Column inner active diameter=2300-2500 mm
Packing length=15-16 m
Total column length=18-19 m

The invention claimed is:

1. A method for producing aniline, comprising:
    a) providing an aqueous solution of o-aminobenzoate, wherein said o-aminobenzoate comprises anthranilate anion and $NH_4^+$ and/or $Na^+$ as cation,
    b) converting said anthranilate anion to aniline by thermal decarboxylation in the presence or absence of a catalyst, and either
    c1) purifying the aniline produced in step b) by distillation if the content of aniline in the aqueous solution obtained in method step b) is above 120 g/l, or
    c2) extracting the aniline obtained in method step b) at least once in an organic solvent before purifying the aniline by distillation if the content of aniline in the aqueous solution obtained in method step b) is not more than 120 g/l.

2. The method of claim 1, wherein said o-aminobenzoate is provided chemically or produced biologically.

3. The method of claim 1, wherein step a) to step c1) or step c2) are run continuously.

4. The method of claim 1, wherein said catalyst is a heterogeneous acid catalyst.

5. The method of claim 1, wherein said catalyst is a heterogeneous base catalyst.

6. The method of claim 1, wherein the extraction of aniline in an organic solvent in step c2) is performed for more than one time for a further pre-concentration of aniline in advance of distillation.

7. The method of claim 1, further comprising recovering the organic solvent used in the extraction of step c2).

8. The method of claim 1, wherein said organic solvent is selected from the group consisting of alcohols, phenols, amides, ethers and aromatic hydrocarbons.

9. The method of claim 1, wherein the $NH_4^+$ cation is recovered as $NH_3$ subsequent to the distillation of step c1) and re-fed to the fermentation of step a).

10. The method of claim 2, wherein said o-aminobenzoate is produced biologically by fermentation of a raw material comprising at least one fermentable carbon substrate using a recombinant microbial host cell capable of converting said raw material comprising a fermentable carbon substrate to o-aminobenzoate by fermentation.

11. The method of claim 10, wherein said recombinant microbial host is removed prior to the subsequent conversion of said anthranilate anion to aniline by thermal decarboxylation in step b), wherein said removed recombinant microbial host preferably is re-fed to the fermentation of step a).

12. The method of claim 10, further comprising a further step e) of re-feeding the water-phase of the extraction performed in step c) and/or re-feeding the water-phase of the distillation performed in step d) to the fermentation of step a).

13. The method of claim 10, wherein the raw material of step a) is selected from the group consisting of sugar beet, sugar cane, starch-containing plants, lignocellulose, glycerol and C1-compounds.

14. The method of claim 10, wherein said fermentable carbon substrate is selected from the group consisting of C-5 monosaccharides, C-6 monosaccharides, disaccharides, and tri-saccharides.

15. The method of claim 10, wherein said recombinant host is selected from the group consisting of bacteria, yeast and fungi.

16. The method of claim 10, wherein said fermentation of step a) is a batch fermentation, a fed-batch fermentation or a continuous fermentation.

17. The method of claim 4, wherein said heterogeneous acid catalyst comprises a zeolite.

18. The method of claim 17, wherein said zeolite comprises zeolite H—Y.

19. The method of claim 5, wherein said heterogeneous base catalyst comprises a layered double hydroxide.

20. The method of claim 19, wherein said layered double hydroxide comprises Mg—Al hydrotalcite.

21. The method of claim 7, wherein the recovering comprises distillation.

22. The method of claim 7, wherein recovered organic solvent is re-fed to step c2).

23. The method of claim 8, wherein said organic solvent comprises an alcohol comprising 1-dodecanol.

24. The method of claim 13, wherein the raw material of step a) comprises a starch-containing plant comprising corn.

25. The method of claim 13, wherein the raw material of step a) comprises a lignocellulose comprising straw, wood, and/or bagasse.

26. The method of claim 13, wherein the raw material of step a) comprises a C1-compound comprising CO.

27. The method of claim 14, wherein said fermentable carbon substrate comprises a C-5 monosaccharide comprising xylose and/or arabinose.

28. The method of claim 14, wherein said fermentable carbon substrate comprises a C-6 monosaccharide comprising glucose, fructose, and/or mannose.

29. The method of claim 14, wherein said fermentable carbon substrate comprises a disaccharide comprising saccharose.

30. The method of claim 14, wherein said fermentable carbon substrate comprises a trisaccharide comprising ketose.

31. The method of claim 15, wherein said recombinant host comprises bacteria comprising *Eschericha coli* strain, a *Corynabacterium* strain and/or a *Pseudomonas* strain.

32. The method of claim 31, wherein said bacteria comprises a *Corynabacterium* strain comprising *Corynabacterium glutamincum*.

33. The method of claim 32, wherein said *Corynabacterium glutamincum* comprises *Corynabacterium glutamincum* ATCC 13032.

34. The method of claim 31, wherein said bacteria comprises a *Pseudomonas* strain comprising *Pseudomonas putida*.

35. The method of claim 34, wherein said *Pseudomonas putida* comprises *Pseudomonas putida* KT2440.

36. A method of using aniline produced by the method of claim 1, comprising converting the aniline to methylenedianiline using formaldehyde in the presence of water and catalyst.

37. A method of using methylenedianiline produced by the method of claim 36, comprising converting the methylenedianiline to methylenediisocyanate using phosgene.

* * * * *